US006928338B1

(12) United States Patent
Buchser et al.

(10) Patent No.: US 6,928,338 B1
(45) Date of Patent: Aug. 9, 2005

(54) DECISION INFORMATION SYSTEM FOR DRUG DELIVERY DEVICES

(75) Inventors: Eric E. Buchser, Grandvaux (CH); Brenda K. Schultz, Minneapolis, MN (US); Brian T. Dummann, Andover, MN (US); Thomas J. Valine, Spring Lake Park, MN (US); Thomas P. Crowley, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 505 days.

(21) Appl. No.: 10/215,464

(22) Filed: Aug. 9, 2002

Related U.S. Application Data
(60) Provisional application No. 60/311,527, filed on Aug. 10, 2001.

(51) Int. Cl.$^7$ .............................................. G06F 19/00
(52) U.S. Cl. ...................... 700/265; 700/281; 700/285; 604/67
(58) Field of Search ................................ 700/264–265, 700/281, 285; 604/67, 66; 128/200

(56) References Cited

U.S. PATENT DOCUMENTS

| | | | | |
|---|---|---|---|---|
| 5,509,404 A | * | 4/1996 | Lloyd et al. | 128/200.14 |
| 5,772,635 A | | 6/1998 | Dastur et al. | |
| 5,915,971 A | | 6/1999 | Ramsay et al. | |
| 6,070,102 A | * | 5/2000 | Hartlaub et al. | 607/31 |
| 6,210,361 B1 | * | 4/2001 | Kamen et al. | 604/82 |
| 6,273,727 B1 | | 8/2001 | Ramsay et al. | |
| 6,740,075 B2 | * | 5/2004 | Lebel et al. | 604/891.1 |
| 2005/0010166 A1 | * | 1/2005 | Hickle | 604/66 |

FOREIGN PATENT DOCUMENTS

| | | |
|---|---|---|
| EP | 0319272 A2 | 6/1989 |
| WO | WO96/36389 | 11/1996 |

OTHER PUBLICATIONS

Altas, Glen, "Tutorial 25: Calculating Mixtures of Local Anesthetic and Morphine for Implantable Intrathecal Pumps", *Pain Digest* (1996), vol. 6, pp. 232–236.

(Continued)

*Primary Examiner*—Kidest Bahta
(74) *Attorney, Agent, or Firm*—Fredrikson & Byron, P.A.

(57) ABSTRACT

Decision information systems, methods, and computer programs for better informing decisions to use multiple drugs in drug delivery devices, including implantable devices, for drug administration. Executable computer programs and logic embodying methods of the invention can calculate consistent multiple drug mixture amounts and drug delivery flow rates. One program accepts user input indicating a desired first drug dose rate, an initial first drug concentration, a desired second drug dose rate, an initial second drug concentration, and the reservoir size of the drug delivery device. The program method calculates a first drug amount and a second drug amount to combine in a mixture as well as a first drug true concentration in the mixture. The drugs can be mixed consistent with the physician's instructions using the program output. The first drug true concentration can be entered into a programmer device as the only drug concentration entered. Another program calculates a consistent first drug, second drug, and diluent amount to be added to a mixture for injection into a fixed flow rate, implantable drug delivery device. Methods preferably output true concentrations and dose rates for all drugs to be added and most preferably show all calculations used to arrive at the flow rate and mixture amount calculations. Yet another program receives a new desired drug dose rate for a previously filled device. The program accepts the existing mixture volume and true drug concentrations for a partially depleted device and calculates a new mixture flow rate to achieve the desired dose rate using the existing mixture. The methods can be implemented as executable computer programs in programmer devices, general purpose computers, servers, handheld computers, and personal digital assistants.

45 Claims, 11 Drawing Sheets

OTHER PUBLICATIONS

Buchser, E., et al., "Computer Assisted Calculation of Drug Mixture Composition for Intrathecal Drug Administration: A Presentation of the e-MICS Software". This article was presented and distributed with the two page poster identified in (3) below at the "Worldwide Pain Conference 2000" conference in San Francisco on Jul. 15-17, 2000.

Buchser, E., et al., "e-MICS Drug Mixture Composition Software" (two-page poster). Presented and distributed at the "Worldwide Pain Conference 2000" in San Francisco on Jul. 15-17, 2000.

* cited by examiner

Fig. 1
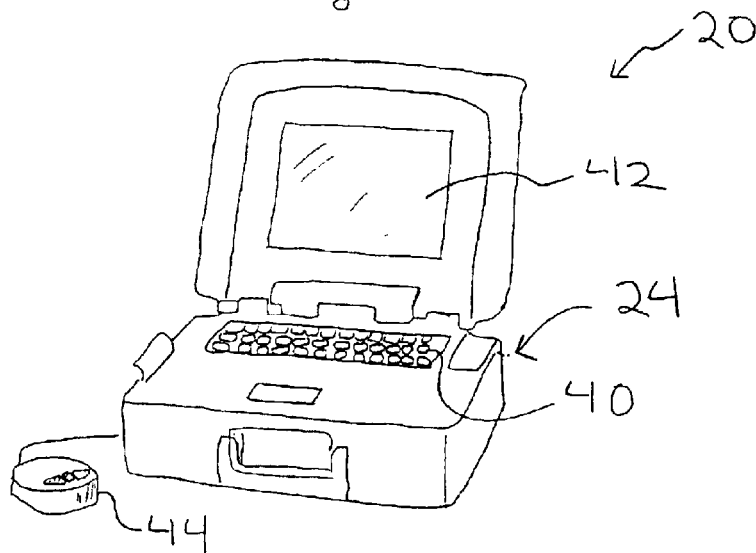
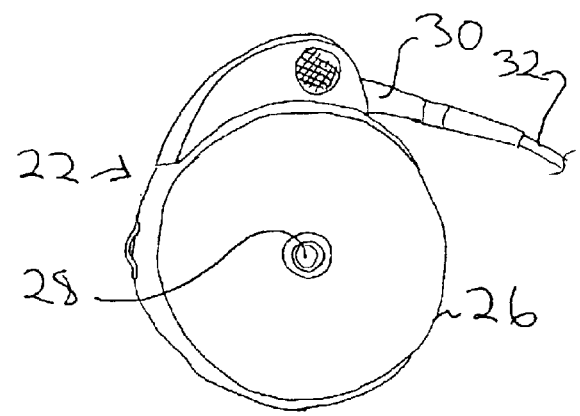
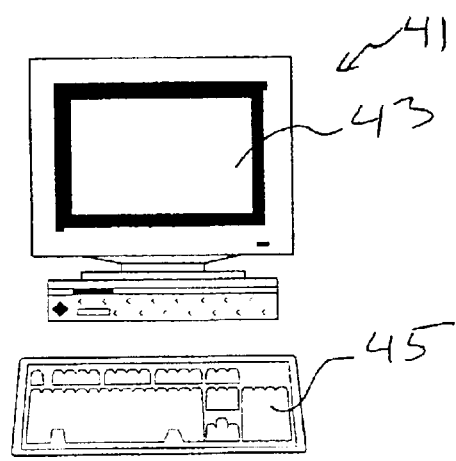

🗒 New calculation

1. Select Pump Flow Rate ⟵204
If the pump has a variable flow rate, then select 'Programmable'. If the pump has a fixed flow rate, then select 'Fixed Rate' and enter the rate

| Pump Flow Rate | ⊙ Programmable | |
|---|---|---|
| | ○ Fixed Rate | ____ mL/day |

⟵202
206   208

2. Select Pump Reservoir Volume
Select a Medtronic pump or other pump reservoir volume. Click on the menu for Medtronic pump volumes, or you can type in a volume of your choice ⟵212

| Pump Reservoir Volume | ⊙ Medtronic pump | 18 mL ▾ |
|---|---|---|
| | ○ Other volume | ____ mL |

⟵210
214

3. Revise Drug List
If you would like to make changes to your drug list, click on the button below

[ Revise your personal drug list ]  ⟵216

4. Enter Drug Information
Enter the drug, concentration, and dosage for 1 or more drugs
- Click on the menu to choose a drug from your drug list, then type in concentration, dose, and choose metrology (mg/ml, mg, etc.) by clicking on the menus
- To remove a drug from this calculation, click on the drug menu and select the blank space 230    232    236

| | Drug 226 | Concentration 228 | Dose/day 234 |
|---|---|---|---|
| 1 | Morphine ▾ | 10 mg/mL ▾ | 3 mg ▾ |
| 2 | Bupivacaine ▾ | 20 mg/mL ▾ | 3 mg ▾ |
| 3 | ▾ | mg/mL ▾ | mg ▾ |
| 4 | ▾ | mg/mL ▾ | mg ▾ |
| 5 | ▾ | mg/mL ▾ | mg ▾ |

238
⟵220

222
224

5. Perform calculation
Click on the button below to calculate

[ 🗒→👥 Perform the calculation ]  ⟵240

Fig. 8A

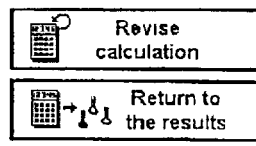

 The math behind the calculations

The drug algorithm states that: 302

$$Caf = \frac{Cai \times Cbi \times Cci \times Cdi \times Cei}{((Cbi \times Cci \times Cdi \times Cei) + R1x(Cai \times Cci \times Cdi \times Cei) + R2x(Cai \times Cbi \times Cdi \times Cei) + R3x(Cai \times Cbi \times Cci \times Cei) + R4x(Cai \times Cbi \times Cci \times Cdi))}$$

If we convert all units to mL and mg: 304

$Caf$ = Final concentration of Drug A
$Cai$ = Initial Concentration of Drug A = 10 mg/mL
$Cbi$ = Initial Concentration of Drug B = 20 mg/mL
$Cci$ = Initial Concentration of Drug C = 1 mg/mL
$Cdi$ = Initial Concentration of Drug D = 1 mg/mL
$Cei$ = Initial Concentration of Drug E = 1 mg/mL
$Ta$ = Dose per day of Drug A = 0.3 mg
$Tb$ = Dose per day of Drug B = 3 mg
$Tc$ = Dose per day of Drug C = 0 mg
$Td$ = Dose per day of Drug D = 0 mg
$Te$ = Dose per day of Drug E = 0 mg
$R1 = Cbf/Caf = Tb/Ta = 10$
$R2 = Ccf/Caf = Tc/Ta = 0$
$R3 = Cdf/Caf = Td/Ta = 0$
$R4 = Cef/Caf = Te/Ta = 0$

Fig. 8B

*If we insert the variables into the equation:* 306

$$Caf = \frac{10 \times 20 \times 1 \times 1 \times 1}{(20 \times 1 \times 1 \times 1) + 10x(10 \times 1 \times 1 \times 1) + 0x(10 \times 20 \times 1 \times 1) + 0x(10 \times 20 \times 1 \times 1) + 0x(10 \times 20 \times 1 \times 1)}$$

*Then, by doing the multiplication first, we have:* 308

$$Caf = \frac{200}{(20) + 10 \times (10) + 0 \times (200) + 0 \times (200) + 0 \times (200)}$$

*Further multiplication gives us the following:* 310

$$Caf = \frac{200}{20 + 100 + 0 + 0 + 0}$$

*Adding together the terms in the denominator:* 312

$$Caf = \frac{200}{120}$$

*Thus, Caf = 1.6667 mg/mL.* 314

*Using the Dose Per Day (converted to mL/day), we can solve for the ratios R1, R2, R3, and R4:* 316

R1 = 3 mL/day/0.3 mL/day = 10
R2 = 0 mL/day/0.3 mL/day = 0
R3 = 0 mL/day/0.3 mL/day = 0
R4 = 0 mL/day/0.3 mL/day = 0

*Using the ratios R1, R2, R3, and R4, we find that:* 318

Cbf = R1 x Caf = 10 x 1.6667 mg/mL = 16.6667 mg/mL
Ccf = R2 x Caf = 0 x 1.6667 mg/mL = 0 mg/mL
Cdf = R3 x Caf = 0 x 1.6667 mg/mL = 0 mg/mL
Cef = R4 x Caf = 0 x 1.6667 mg/mL = 0 mg/mL

Fig. 8C

Before calculating the volume, add 2 mL to the reservoir volume to account for the loss of liquid during the process of injecting the mixture into the pump. This means that 18 mL + 2 mL = 20 mL. Using the following equations:

$Vai = (Caf/Cai) \times Volume$
$Vai = (1.6667\ mL/mg/10mL/mg) \times 20\ mL$
$Vai = 3.3333\ mL$
$Vbi = (Cbf/Cbi) \times Volume$
$Vbi = (1.6667\ mL/mg/20\ mL/mg) \times 20\ mL$
$Vbi = 16.6667\ mL$
$Vci = (Ccf/Cci) \times Volume$
$Vci = (0\ mL/mg/1\ mL/mg) \times 20\ mL$
$Vci = 0\ mL$
$Vdi = (Cdf/Cdi) \times Volume$
$Vdi = (0\ mL/mg/1\ mL/mg) \times 20\ mL$
$Vdi = 0\ mL$
$Vei = (Cef/Cei) \times Volume$
$Vei = (0\ mL/mg/1\ mL/mg) \times 20mL$
$Vei = 0\ mL$ The mixture's daily flow rate is:
$Ta/Caf = 0.3\ mL/day/1.6667\ mg/mL = \mathbf{0.18\ mL/day}$ We want to refill the pump when 2 mL of the mixture remains within the reservoir. Thus:
Reservoir Volume − 2 mL = Refill Reservoir Volume
18 mL − 2 mL = 16 mL.

In order to calculate the number of days that will elapse before the next refill, we use the following calculation:
Refill Reservoir Volume/Flow Rate = Refill Interval
16 mL/0.18 mL/day = 88 days

 

▦ Revise calculation  204

1. Select Pump Flow Rate
If the pump has a variable flow rate, then select 'Programmable'. If the pump has a fixed flow rate, then select 'Fixed Rate' and enter the rate  202

| Pump Flow Rate | ⦿ Programmable |  |  |
|---|---|---|---|
|  | ○ Fixed Rate | 0.25 | mL/day |

208, 206, 402

2. Select Pump Reservoir Volume
Select a Medtronic pump or other pump reservoir volume. Click on the menu for Medtronic pump volumes, or you can type in a volume of your choice  212

| Pump Reservoir Volume | ○ Medtronic pump | 18 mL |
|---|---|---|
|  | ○ Other volume |  mL |

210, 214

3. Revise Drug List
If you would like to make changes to your drug list, click on the button below

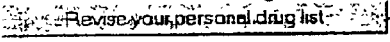 216

4. Enter Drug Information
Enter the drug, concentration, and dosage for 1 or more drugs
- Click on the menu to choose a drug from your drug list, then type in concentration, dose, and choose metrology (mg/ml, mg, etc.) by clicking on the menus
- To remove a drug from this calculation, click on the drug menu and select the blank space  230, 236

| | Drug 226 | Concentration 228 | Dose / day 234 | 238 |
|---|---|---|---|---|
| 1 | Morphine | 10 | mg/mL | 0.3 | mg |
| 2 | Bupivacaine | 20 | mg/mL | 3 | mg |
| 3 |  |  | mg/mL |  | mg |
| 4 |  |  | mg/mL |  | mg |
| 5 |  |  | mg/mL |  | mg |

222, 224, 232, 404, 220

5. Perform calculation
Click on the button below to calculate

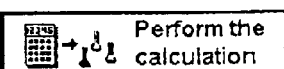 240

Fig. 10

  Calculation results    _420_

Notes: All volumes are rounded to the nearest tenth (0.1) mL
All non-bolus concentrations are rounded to one decimal place Composition of the drug mixture: The volume of the drug mixture is 20 mL (18 mL reservoir volume + 2 mL to account for loss in syringe/tubing)

1. 5.6 mL of Saline - note: saline was added by the calculator because you are using a fixed rate pump
2. 2.4 mL of Morphine [ 10 mg/mL ]
3. 12 mL of Bupivacaine [ 20 mg/mL ]

_424_  _422_

Note: If saline appears twice in the list, that is because you added saline as one of the "drugs" in the mixture, and then the calculator added saline in order to match the pump's flow rate

_426_

Do not inject more than 18 mL into the pump reservoir.

Refill interval: 64 days
Note: The refill interval is based on refill volume less 2 mL to ensure adequate time between refills and optimal pump function

_262_

Flow Rate: 0.3 mL/day    _266_

_264_

The true concentration of drugs in the mixture and dose/day:
  Morphine      1.2 mg/mL    0.3 mg/day  _268_
  Bupivacaine   12 mg/mL     3 mg/day    _272_

_265_

_270_

DECISION INFORMATION SYSTEM FOR DRUG DELIVERY DEVICES

RELATED APPLICATION

The present invention is related to and claims priority to U.S. Provisional Patent Application Ser. No. 60/311,527, filed Aug. 10, 2001 entitled MEDICINE CONCENTRATION CALCULATION SOFTWARE, herein incorporated by reference in entirety.

FIELD OF THE INVENTION

The present invention is related generally to medical devices. More specifically, the present invention is related to implantable drug delivery devices. The present invention includes decision information systems for programming and filling implantable drug delivery devices.

BACKGROUND OF THE INVENTION

Implantable drug delivery devices are increasingly used to manage pain, spasticity, cancer, and other medical conditions in patients. Implantable drug delivery devices, also referred to as implantable drug delivery pumps, are currently used to administer therapeutic agents to various locations within the body. Some drug delivery devices have variable volumetric flow rates, adjustable through an external programmer device. Other implantable drug delivery devices have fixed volumetric flow rates, but can be activated and deactivated externally. Still other drug delivery devices have fixed volumetric flow rates and are not adapted to be controlled from outside of the body.

Experienced physicians have begun to administer combinations of two or more drugs. Many physicians choosing to administer drug combinations via implanted programmable pumps use clinical judgment rather than consistent, accurate calculation to determine the daily dose of each drug. Where calculations are done, they may be ad hoc, as they are not supported by either the drug manufacturers or the pump manufacturers.

The physicians administering multiple drugs through the implantable pumps thus use clinical judgment in mixing drugs and filling the implantable pump reservoirs. The physicians choosing the multiple drug route must also often use pump programmer devices designed to administer only a single drug in variable quantities. Specifically, the programmer devices currently assist a treating physician in administering the desired dose of a single drug, but provide no assistance in the proper administration of a mixture of drugs.

What would be desirable is a decision information system for aiding physicians who elect to administer multiple drugs for a given therapy. What would be advantageous are decision information systems to provide physicians with consistent methodologies and feedback to aid the physician in programming drug delivery programmer devices and filling implantable drug reservoirs consistently with the intent of the treating physician.

SUMMARY OF THE INVENTION

The present invention provides decision information systems, methods, and computer programs for administering multiple drugs through implantable drug delivery devices. Some aspects of the system support implantable drug delivery devices having adjustable flow rates while other aspects of the system support fixed flow rate implantable drug delivery devices. The methods provided can be used with both non-programmable implantable drug delivery devices as well as programmer devices for use with implantable drug delivery devices. The present invention can also be used with other drug devices, such as those in which only a catheter extends into the patient, and the reservoir remains external to the patient. The present invention can be used with two or more drugs in a mixture together with diluent in some situations. A preferred embodiment of the invention supports at least 5 drugs and allows for user entry of drug names.

One decision information system according to the present invention can be used in a system including an implantable drug delivery device having an adjustable flow rate, a drug delivery device programmer device for setting the adjustable flow rate via telemetry, and a programmable computer. In a typical system, the adjustable volumetric flow rate is set by the programmer device through telemetry, with the human user setting the volumetric flow rate indirectly through setting of a desired drug dose rate. A method according to the present invention can be implemented as computer logic or a computer program executing within the programmable computer. In some embodiments, the programmable computer is a general purpose computer, handheld computer, or palm-held computer. In other embodiments, the programmable computer is the same device as the programmer device for setting the adjustable flow rate via telemetry.

One method, which can be used with adjustable flow rate devices, includes entering into a computer device a desired dose rate and initial concentration for a first drug, a desired dose rate and initial concentration for a second drug, and either a known reservoir volume for the implantable drug delivery device or a desired total mixture volume. One of the drugs can be selected as the "reference" drug. The reference drug is the drug that the programmer device will use to program the drug delivery device. The reference drug is typically the only drug the programmer device is aware of. The method can further include executing a computer program in the computer to calculate a first drug amount and a second drug amount to be added to the mixture, wherein the first and second drug amounts are consistent with the desired first and second drug dose rates when delivered at a proper mixture flow rate. When the first and second drugs are the only drugs to be added to the mixture, the first and second drug amounts are preferably sufficient to substantially fill the reservoir. The method can further calculate a first drug true concentration in the drug mixture. The first drug true concentration can be output to the user, along with the flow rate and date of next refill.

The calculated first drug true concentration in the mixture can then be entered into the programmer device along with the first drug desired dose rate. The first and second drugs can be mixed in the amounts calculated by the computer program and injected into the drug delivery device reservoir. The programmer device can also be used to transmit a flow rate to the implantable device to satisfy the first drug desired dose rate.

Some computer program methods according to the present invention, which can be used with adjustable flow rate devices, further output the first drug and second drug dose rates to the user. Some methods also calculate volumetric flow rates for the first drug and the second drug. Other methods further comprise calculating and outputting the second drug true concentration in the mixture. In preferred embodiments, the mathematical calculations used to generate the intermediate and final outputs are output and visually displayed for user inspection. In preferred embodiments of the present invention, three, four, five, or more drugs may also be added and supported in a manner similar to the first and second drugs, described above.

Another aspect of the present invention provides a computer program method for determining a new daily drug dose for one drug without changing the mixture in the implantable device. The program can receive the true concentration of each drug in the mixture as well as the existing mixture volume remaining in the implantable device. In a preferred embodiment, the program receives the true concentration and existing mixture volume by retrieving previously stored values. A preferred method retrieves the previously calculated and stored true concentrations in the mixture and calculates the remaining volume in the device using the previously calculated total flow rate and the time elapsed since the previous fill.

The program can also receive the desired new dose rate for one of the drugs in the mixture. The program can then calculate and output the new dose rate for the reference drug, the estimated refill interval and/or date, and the dose rates for all drugs in the mixture. Some program methods calculate and output the proper volumetric flow rate for the implantable device. A programmer unit can then be used to transmit the new reference drug flow rate and/or the new volumetric flow rate to the implantable device.

The present invention also supports fixed flow rate implantable drug delivery devices. In a fixed flow rate aspect of the present invention, the fixed flow rate, total desired mixture volume, desired dose rate, and initial concentration for a first and a second drug are obtained from the user through the computer program. The computer program executes logic to determine the proper amounts of the first and second drug to be added to the mixture to be injected into the implantable drug delivery device. The required amount of saline or other diluent is also preferably calculated and output to the user, with the saline or other diluent to be added to the mixture of the first and second drugs. The method preferably warns the user through the computer output when a desired drug dose rate is not possible due to flow rate limitations. The present invention specifically includes methods for determining the correct amounts of a first and a second drug to contribute to a drug mixture for supplying an implantable drug infusion device.

The present invention specifically includes the above discussed methods, computer programs executing these methods, computer devices executing the computer programs, and computer readable media storing executable computer programs embodying the methods of the present invention. Computer servers executing the present invention program methods for client computer devices over networks, that can include the Internet, are also within the scope of the invention.

DESCRIPTION OF THE DRAWINGS

FIG. 1 is a schematic view of a drug delivery system including an implantable drug delivery device, a programmer device for programming the implantable drug delivery device through a telemetry head, and a computer device for providing information support;

FIG. 6 is a computer display of a data entry screen for obtaining data from a user in a computer implementation of the present invention;

FIGS. 8A–8C are computer displays showing the calculations generating the outputs of FIG. 7;

FIG. 9 is a computer display of a data entry screen for a fixed flow rate implantable drug delivery device; and FIG. 10 is a computer display of a data output screen having results for the fixed flow rate pump screen of FIG. 9.

DETAILED DESCRIPTION OF THE PREFERRED EMBODIMENTS

Figure 2:
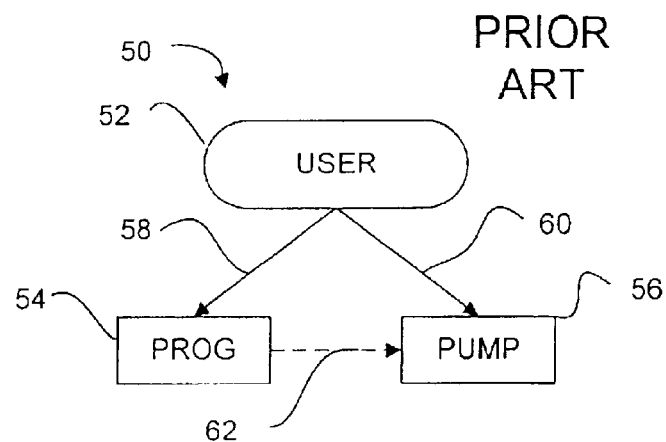
FIG. 2 is a simplified data flow diagram of a prior art system of user interaction with a programmer device and an implantable drug delivery device.

The following detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described above are merely for illustrative purposes, and are not intended to limit scope of the invention as defined in the claims which follow.

FIG. 1 illustrates a system 20 for programming an implantable drug delivery device 22. Drug delivery device 22 may also be referred to as a drug infusion device or a drug pump. Examples of drug delivery devices include the SynchroMed® programmable drug delivery pump, manufactured by Medtronic. Another example of an implantable drug delivery pump is the IsoMed® implantable device, a fixed rate implantable drug delivery pump, also manufactured by Medtronic. Drug delivery device 22 can include a housing 26 and a drug delivery catheter 32 coupled to housing 26 via a coupling 30. Drug delivery device 22 also has a septum 28 for allowing replenishment of the drug supply contained within the device. Drug delivery device 22 typically has a defined reservoir size within, which can be on the order of about 20 milliliters in some embodiments, and 60 milliliters in other embodiments. Drug delivery devices such as drug delivery device 22 typically have a fluid delivery rate which is adjustable or settable through telemetry. The rate, as seen by device 22, is typically a volumetric flow rate. Some embodiments of the present invention are also adapted to work with implantable drug deliver devices having a fixed flow rate. Such drug delivery devices typically do not communicate with a programmer unit.

System 20 also includes programmer device 24 for communicating with implantable drug device 22. Programmer device 24 can include a data entry component, for example, keyboard 40. Device 24 can also include a display 42 and can be coupled to a telemetry head or transceiver 44. Telemetry head 44 typically communicates with implantable drug delivery device 22 through radio frequency signals. In some systems, programmer device 24 is a general purpose computer coupled to a telemetry head. In other embodiments, programmer device 24 is a computing device which has been specially adapted to program and communicate with an implantable drug delivery device. Programmer device 24 can be capable of executing computer programs generally as well as the special purpose computer programs adapted to communicate with and control implantable drug delivery device 22.

A computer device 41 is also illustrated, having a display 43 and a data entry keyboard 45. Computer device 41 can execute programs embodying the present invention. Computer 41 can be used to provide information to fill drug delivery device 22 and program programmer device 24. In some systems, computer 41 is a general purpose computer. In other systems, computer 41 is a hand held computer or personal digital assistant (PDA).

FIG. 2 illustrates a simplified, prior art data flow diagram 50, illustrating the data flow in previous programmer and implantable drug pump systems. Data flow diagram 50 illustrates a user 52 communicating with both an implantable drug pump or drug infusion device 56 and a programmer device 54. Programmer device 54 may be seen to communicate with drug infusion pump 56 through telemetry data flow 62. User 52 may be seen to communicate with programmer device 54 through data flow link 58 and with pump 56 through data flow link 60.

As previously discussed in the background section, pump 56 and programmer device 54 are typically approved to administer only a single drug at any one time. The pump and programmer device are typically government regulated, and approved to only deal with administration of a single drug at any one time. In one example, pump 56 may be adapted to deliver an adjustable volumetric flow rate of drug per day. In this example, programmer device 54 may be adapted to select a single drug, and receive the desired dose rate for the drug as well as the initial concentration of the drug for supplying the pump. The programmer device can then calculate the proper volumetric flow rate for pump 56 and transmit that volumetric flow rate to pump 56. The volumetric flow rate may be transmitted either as a volumetric flow rate or as a raw, scaled value understood as a volumetric flow rate by pump 56.

Data flow link 58 thus represents the entry by user 52 of the desired drug dose rate and available drug concentration. Data flow link 60 represents the physical interaction between user 52 and the pump 56, specifically, the replenishment of the pump reservoir with the drug supplied by the user. In prior art systems, programmer device 54 is adapted to program the use of only a single drug at any one time. In prior art systems utilizing fixed rate implantable drug delivery devices, programmer device 54 may not be utilized at all, with the only interaction being the filling of pump 56 with a drug through interaction 60. In some prior art systems, programmer devices may be used to communicate with the implantable drug delivery devices even though the drug delivery flow rate is fixed.

Figure 3:
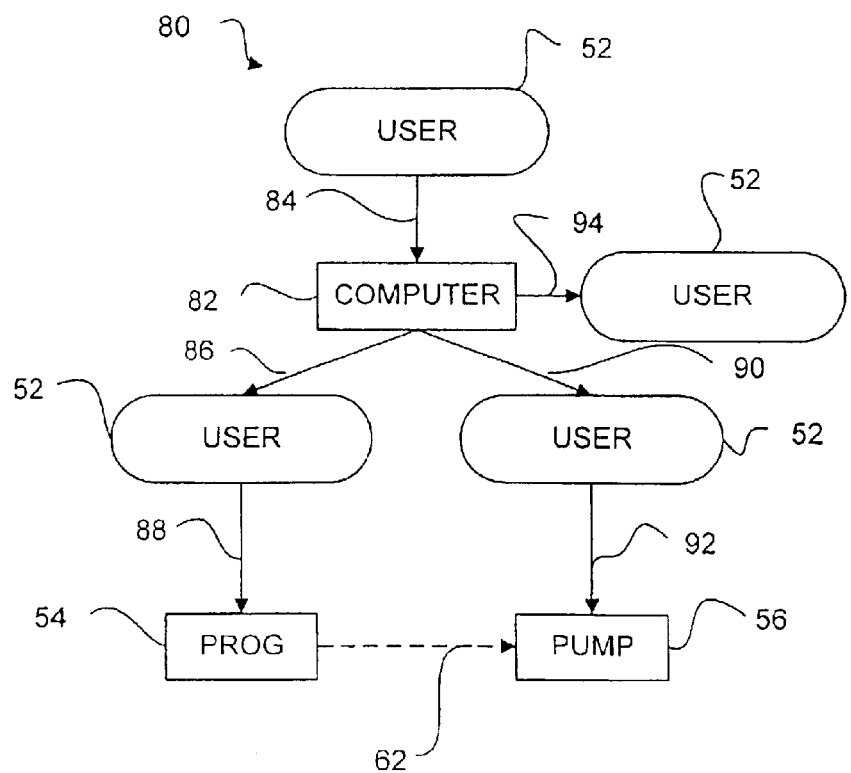
FIG. 3 is a simplified data flow diagram of a system according to the present invention for interfacing with a programmer device, filling an implantable drug delivery device, and providing calculations and feedback to the user.

FIG. 3 illustrates a simplified data flow diagram 80 according to one embodiment of the present invention. User 52, programmer device 54, pump 56, and telemetry link 62 are as previously described with respect to FIG. 2. In a preferred embodiment of the present invention, methods and systems utilizing the present invention can be used with existing, approved programmer devices and pumps. In situations where a treating physician intends to use drug mixtures regardless of the lack of government approval, and regardless of the instructions of the manufacturers of the program devices and drug delivery pumps, the present invention provides an improved method and system for informing the treating physicians.

User 52 can interact with computer 82 through data flow link 84. Computer 82 can be a general purpose computer, special purpose computer, handheld computer, palm-sized computer, or a computer functionality residing within programmer device 54. Computer 82 need only be capable of executing a computer program and interacting with user 52 in order to implement the present invention. In use, user 52 may input information about two or more drugs to be supplied to pump 56. The user will be provided with useful information about the use of the two or more drug mixture with programmer device 54 and pump 56.

In one example of the invention, user 52 provides the desired dose rate and starting or initial concentrations of the first and second drugs available to be supplied to the pump. The initial concentration of the drugs refers to the concentration of the drugs as they are available from the drug manufacturer. The user can also provide the computer with the known reservoir volume of pump 56. The user may optionally provide a bolus definition through data flow link 84. User 52 will typically use a computer keyboard in order to enter data into computer 82.

Computer 82 can then execute a computer program to calculate the proper output to enter into the programming device, the proper amounts of drugs to be supplied into the pump reservoir, as well as additional information to be provided to the user. Computer 82 can provide outputs at 86 to be entered by user 52 at 88 into programmer device 54. Examples of computer program outputs intended for the programmer device include a first drug true concentration in the mixture and the first drug dose rate to be entered into the programmer device. The first drug may also be referred to as the "reference drug," and can be selected from any of the drugs entered into the mixture, to be presented to the programmer device as the only drug to be programmed into the device. The data flow link at 88 thus typically includes only the first drug true concentration in the mixture and the desired dose rate for the first drug. As previously discussed, the programmer device can convert the first drug true concentration and desired dose rate into a volumetric or scaled flow rate and transmit this flow rate to pump 56 via telemetry link 62.

Computer 82 can also output data through data flow link 90 data intended for user interaction with pump 56, represented at 92. Examples of data output for the pump are the first drug amount and second drug amount to be added to fill the reservoir of pump 56. The first and second drug amounts to be added are calculated so as to satisfy the relative desired dose rates of both the first and second drugs as specified by the user. The first and second drug amounts said to be "consistent" with the desired dose rates if there exists a "proper" flow rate, the flow rate at which the drugs in the mixture are delivered at the desired dose rates. The first and second drug fill amounts, together with any diluent amount, are also preferably calculated to substantially fill the reservoir of the pump, where only two drugs are used in the mixture. The total amounts of all drugs and diluents should substantially fill the reservoir of the pump in any case. In some methods a total desired mixture volume is used in place of the reservoir volume. The desired total mixture volume may be greater or less than the reservoir size.

Computer 82 can also input data indicated by data link 94 to provide additional information to the user. The additional information can provide decision related information to the treating physician. The information provided by data link 94 is typically not information indicating any degree of efficacy or safety, as the treating physician has elected to combine drugs in an unapproved mixture. Information provided at 94 can provide the true concentrations and dose rates for each of the drugs in the mixture, the estimated refill interval at the dose rates, as well as the display of the calculations used to arrive at the fill amounts, true concentrations, dose rates, and flow rate to result at the pump.

Figure 4:
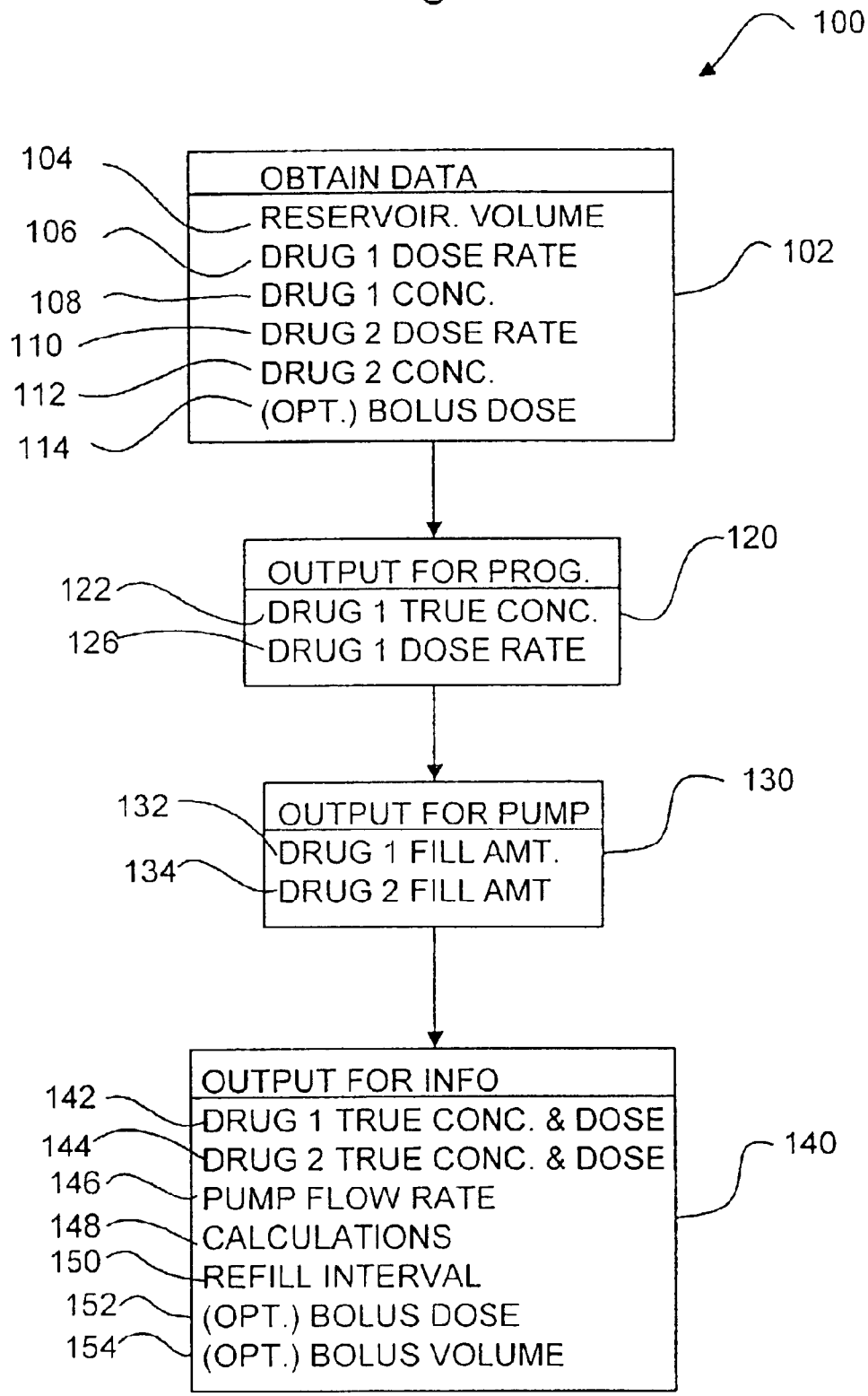
FIG. 4 is a flowchart of a decision information providing method for programming a drug delivery device programmer device and filling an implantable drug delivery device with two or more drugs.

FIG. 4 illustrates a method 100 according to the present invention which can be used with drug delivery devices having adjustable or settable flow rates. Method 100 illustrated by the flow chart may be divided into a step 102 for obtaining information from the user, a step 120 for outputting calculated results to be entered into the programmer device, output results 130 to be utilized to enter or supply drugs to the drug pump reservoir, and output results 140 to supply the user with information as to the mathematical and physical results of their decision and data entry.

In step 102, data is obtained from the user and entered into the computer program in order to support the treating physician's decision to combine drugs in the drug delivery device. Step 102 can include entry of the drug delivery device reservoir volume or total mixture desired volume at 104, a first drug desired dose rate at 106, a first drug initial concentration at 108, a second drug desired dose rate at 110, and a second drug initial concentration at 112. In some embodiments, a desired bolus dose for the first drug is also entered in step 102 at 114.

In step 120, the results of the computer program intended for entry into the programmer unit are output, for example, through the computer display, network, and/or printout. The output of step 120, as well as the other outputs according to the present invention, can also be saved to disk, printed out, and e-mailed, for example, to a pharmacy. Output step 120 can include the output of the first drug true concentration in the mixture at 122, as well as the first drug desired dose rate, typically simply passed through from the entered dose rate supplied by the user in step 102. In step 130, the computer program can output information to be utilized by the user to properly fill the reservoir of the drug delivery device. The first drug amount to add is indicated at 132 and the second drug amount to add is indicated at 134. First and second drug fill amounts 132 and 134 typically have units of milliliters and are sufficient to fill the reservoir of the implantable drug delivery device. Where more than two drugs are used, the total volume of all the drugs to be entered should be sufficient to fill the drug reservoir. In one embodiment, the total volume of drugs indicated to be added at step 130 slightly exceeds the capacity of the reservoir, to allow for loss during filling. In one embodiment, the sum volume of drugs indicated to be added in step 130 exceeds the volume of the reservoir by 2 milliliters.

In step 140, information can be provided to the user to inform the user as to the physical, although not medical, results of their decision to combine drugs. The first drug true concentration and dose rate can be output at 142 and the second drug true concentration and dose rate output at 144. The desired pump flow rate can be output at 146 and the steps of all calculations used to arrive at the results of the method shown at 148. The refill interval can also be provided at 150. In methods including a bolus calculation, the bolus dose for all drugs can be output at 152 as well as the bolus volume at 154.

Figure 5:
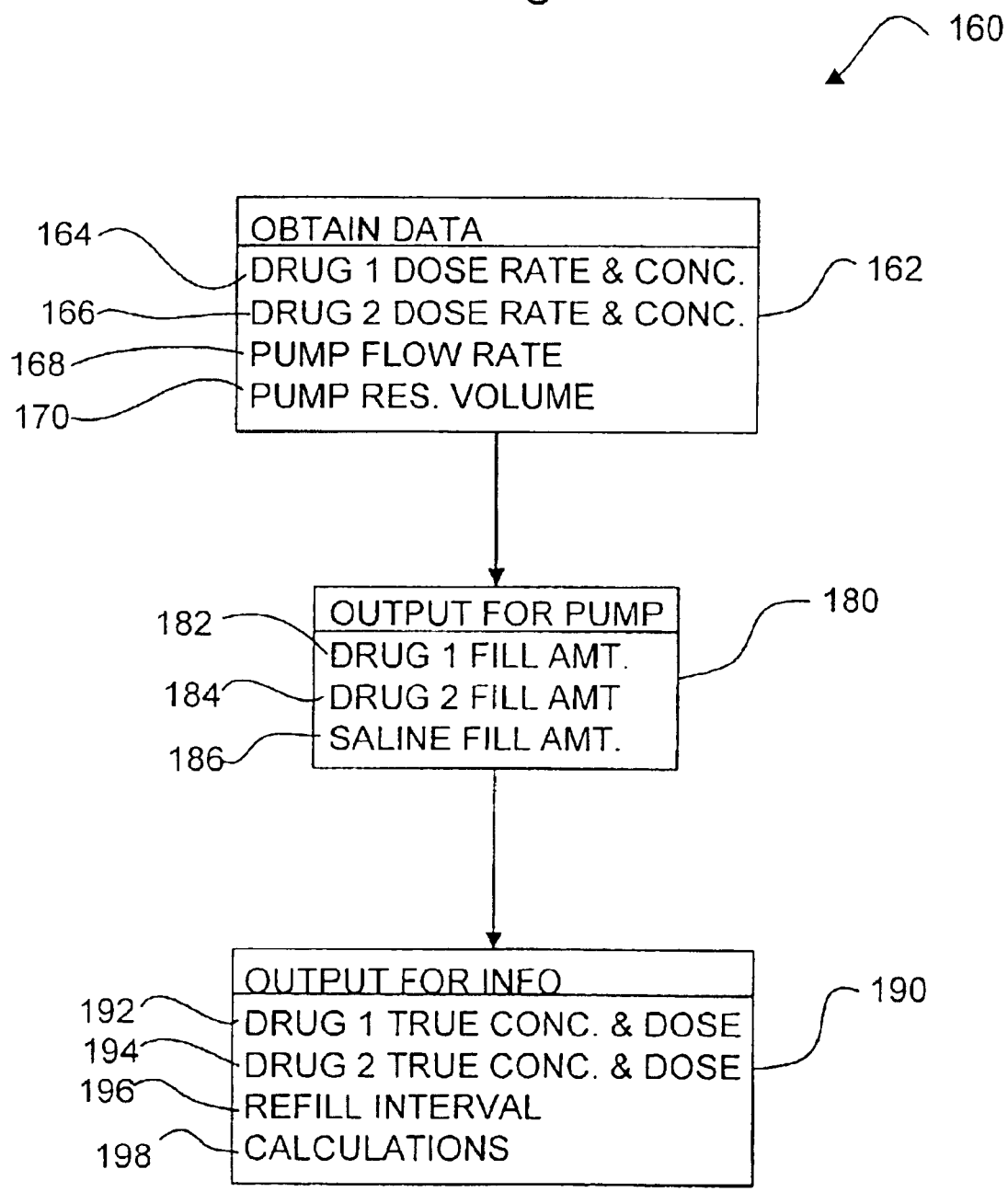
FIG. 5 is a flowchart of a decision information providing method for filling a fixed flow rate implantable drug delivery device.

FIG. 5 illustrates a method 160 according to another embodiment of the present invention, suitable for use with fixed rate implantable drug delivery devices. Method 160 may be divided into a first step 162 for obtaining information from the user, an output step 180 for outputting information to the user to be used in interaction with the pump directly, and an information output step 190 for better informing the user as to the physical, albeit not medical, consequences of their decision to combine drugs in the drug pump.

In data entry step 162, the first drug desired dose rate and initial concentration can be selected at 164 and entered into the computer as can the second drug desired dose rate and initial concentration at 166. The pre-existing, fixed drug device flow rate may be entered at 168 and the pump reservoir volume or desired total drug mixture volume entered at 170.

In data output step 180, the results of the computer program can be output to the user for use in interacting with the pump. The first drug amount to be added to the mixture can be output at 182 and the second drug amount to be added to the mixture output at 184. As the drug delivery device flow rate is fixed, it may be necessary to dilute the mixture with saline or other diluent in order to avoid supplying too high a dose rate of either drug to the patient. For this reason, a saline or diluent amount to be added to the mixture is indicated at 186. In some calculations, the saline or diluent amount will be zero.

In step 190, information is provided to the user in order to better inform the user. The first drug true concentration and dose rate can be provided at 192 as can the second drug true concentration and dose rate at 194. The estimated refill interval can be output at 196. The calculations used to provide all of the data output in method 160 can be displayed at 198. As previously discussed, the data entered and data output in method 160 and other methods can be permanently saved for future reference or re-use, printed out, integrated into a pharmacy ordering system, and/or e-mailed, for example, to a pharmacist.

FIG. 6 illustrates a user interface display 200 of one embodiment of the invention, implemented in the Java programming language for allowing data entry, calculation, and display using general purpose computers coupled to networks. Some methods according to the present invention include computer servers executing programs to serve client computer devices over networks, which can include the Internet. The user interface in FIG. 6 is but one example of the invention. Implementation of the present invention using hand held computers, Palm™ computers, and personal digital assistants are explicitly within the scope of the present invention. User interface 200 may be subdivided generally into a select pump flow rate portion 202, a select pump reservoir volume portion 210, a revise drug list portion 216, a drug entry portion 220, as well as a perform calculation button 240.

In select pump flow rate portion 202, the pump flow rate may be selected as either a programmable pump rate at 204 or a fixed flow rate at 206, with the fixed flow rate indicated and enterable at 208. The pump reservoir volume may be selected from a pull down list at 212 or entered in a free format field at 214.

An invitation to revise a previously entered drug list is provided at 216. Display 200 illustrates drug entry portion 220 as it appears when the drug list revision has been selected at 216. Drug entry portion 220 includes generally a drug name column 226, an initial concentration column 228, and a desired dose rate column 234. In drug name column 226, drug names may be selected from previously entered pull down lists, with Morphine being shown at 222 and Bupivacaine indicated at 224. In some embodiments, users are allowed to enter new drug names into the pull down lists. In concentration column 228, a numerical concentration is shown at column 230 and the units or metrology indicated in column 232, as being either milligrams per milliliter or micrograms per milliliter. In the desired dose rate column 234, the numerical desired dose rate is indicated at column 236 and the selected units or metrology indicated in column 238, indicated as being either milligrams or micrograms. After the data has been obtained from the user and entered into the computer, the calculation can be performed by toggling the button as indicated at 240.

Figure 7:
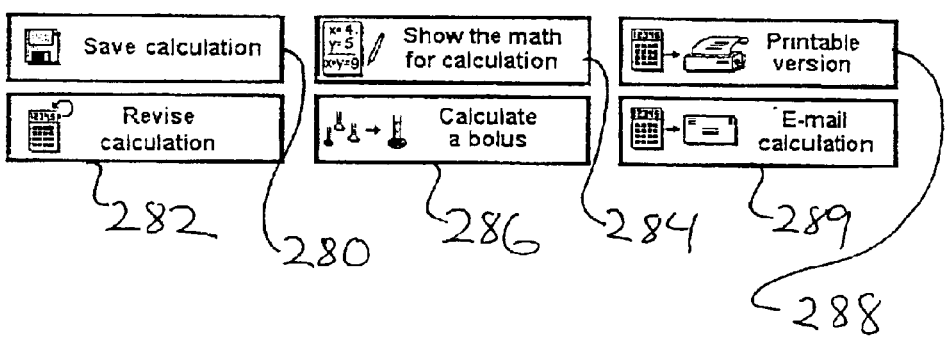
FIG. 7 is a computer display of a data output screen having results based on the data obtained from FIG. 6.

FIG. 7 illustrates the calculation results in user display or output 250. Display 250 may be seen to include a true concentration and initial concentration portion 252 including a first drug volume to be added to the mixture at 254, an initial concentration for the first drug at 256, a second drug amount to be added to the mixture at 258, and the second drug initial concentration at 260. The refill interval is displayed at 262 as well as the desired flow rate at 264.

Output portion 265 includes the first drug true concentration in the mixture at 266 and the first drug dose rate at 268. Similarly, the second drug true concentration in the mixture is indicated at 270 and the second drug dose rate indicated at 272. User instructions are provided at 274, indicating the true concentration of one drug, termed the reference drug, as well as the desired dose rate to be entered into the programmer device. The desired dose rate is typically passed through from the user entered desired dose rate in one embodiment of the invention.

Display 250 thus provides the user with both the amounts of the drugs to be added to the mixture to fill the reservoir as well as the physical, albeit not medical, results of the user entered data. In a preferred embodiment of the present invention, the user can also save the calculation at 280, revise the calculation at 282, show the math for the calculation at 284, generate a printable version at 288, and e-mail the calculation at 289. In some embodiments, the user may also calculate a bolus at 286.

FIGS. 8A–8C illustrate the calculations displayed as a result of the user selecting the "show the math for calculation" button at 284 in FIG. 7. The calculation results are shown generally in display 300. Display 300 may be subdivided into portions for discussion. Button 292 allows for revising the calculation and button 294 allows for returning to the results.

In display portion 302, the algorithm for calculating the final concentration of the first drug is shown to the user:

$$Caf = \frac{Cai \times Cbi \times Cci \times Cdi \times Cei}{(Cbi \times Cci \times Cdi \times Cei) + R1 \times (Cai \times Cci \times Cdi \times Cei) + R2 \times (Cai \times Cbi \times Cdi \times Cei) + R3 \times (Cai \times Cbi \times Cci \times Cei) + R4 \times (Cai \times Cbi \times Cci \times Cdi)}$$

In portion 304, the meaning of the terms used in portion 302 is more fully explained as is the physical value of these terms as input by the user previously:
If we convert all units to mL and mg:
  Caf=Final concentration of Drug A
  Cai=Initial Concentration of Drug A=10 mg/mL
  Cbi=Initial Concentration of Drug B=20 mg/mL
  Cci=Initial Concentration of Drug C=1 mg/mL
  Cdi=Initial Concentration of Drug D=1 mg/mL
  Cei=Initial Concentration of Drug E=1 mg/mL
  Ta=Dose per day of Drug A=0.3 mg
  Tb=Dose per day of Drug B=3 mg
  Tc=Dose per day of Drug C=0 mg
  Td=Dose per day of Drug D=0 mg
  Te=Dose per day of Drug E=0 mg
  R1=Cbf/Caf=Tb/Ta=10
  R2=Ccf/Caf=Tc/Ta=0
  R3=Cdf/Caf=Td/Ta=0
  R4=Cef/Caf=Te/Ta=0

Referring now to FIG. 8B, display portion 306 illustrates the result of substituting the physical values provided by the user into the equation provided at 302:
If we insert the variables into the equation:

$$Caf = \frac{10 \times 20 \times 1 \times 1 \times 1}{(20 \times 1 \times 1 \times 1) + 10 \times (10 \times 1 \times 1 \times 1) + 0 \times (10 \times 20 \times 1 \times 1) + 0 \times (10 \times 20 \times 1 \times 1) + 0 \times (10 \times 20 \times 1 \times 1)}$$

In display portions 308, 310, and 312, the intermediate results of the algorithm are shown, with the final result for the true concentration of the first drug displayed in display portion 314.

Then, by doing multiplication first, we have:

$$Caf = \frac{200}{(20) + 10 \times (10) + 0 \times (200) + 0 \times (200) + 0 \times (200)}$$

Further multiplication gives us the following:

$$Caf = \frac{200}{20 + 100 + 0 + 0 + 0}$$

Adding together the terms in the denominator:

$$Caf = \frac{200}{120}$$

Thus, Caf=1.6667 mg/mL.

In display portion 316, the desired doses per day for the second, third, and fourth drugs can be normalized to the dose per day for the first drug in ratios R1–R4:
Using the Dose Per Day (converted to mL/day), we can solve for the ratios R1, R2, R3, and R4:

R1=3 mL/day/0.3 mL/day=10

R2=0 mL/day/0.3 mL/day=0

R3=0 mL/day/0.3 mL/day=0

R4=0 mL/day/0.3 mL/day=0

In display portion 318, the desired and resultant concentrations of the second and subsequent drugs in the mixture are displayed:
Using the ratios R1, R2, R3, and R4, we find that:

Cbf=R1×Caf=10×1.6667 mg/mL=16.6667 mg/mL

Ccf=R2×Caf=0×1.6667 mg/mL=0 mg/mL

Cdf=R3×Caf=0×1.6667 mg/mL=0 mg/mL

Cef=R4×Caf=0×1.6667 mg/mL=0 mg/mL

Referring now to FIG. 8C, display portion 320 illustrates amounts of each drug to be added to the mixture. The total volume to be created has been set to a small amount, here being 2 milliliters, over the reservoir volume, in order to account for loss of liquid during injection:
Before calculating the volume, add 2 mL to the reservoir volume to account for the loss of liquid during the process of injecting the mixture into the pump. This means that 18 mL+2 mL=20 mL. Using the following equations:

$Vai=(Caf/Cai) \times \text{Volume}$ $Vai=(1.6667\ mL/mg/10mL/mg) \times 20\ mL$ $Vai=3.3333\ mL$ $Vbi=(Cbf/Cbi) \times \text{Volume}$ $Vbi=(1.6667\ mL/mg/20\ mL/mg) \times 20\ mL$ $Vbi=16.6667\ mL$ $Vci=(Ccf/Cci) \times \text{Volume}$ $Vci=(0\ mL/mg/1\ mL/mg) \times 20\ mL$ $Vci=0\ mL$ $Vdi=(Cdf/Cdi) \times \text{Volume}$ $Vdi=(0\ mL/mg/1\ mL/mg) \times 20\ mL$ $Vdi=0\ mL$ $Vei=(Cef/Cei) \times \text{Volume}$ $Vei=(0\ mL/mg/1\ mL/mg) \times 20\ mL$ $Vei=0\ mL$ In display portion 322, the volumetric flow rate of the mixture to be administered by the drug delivery device is displayed:

The mixture's daily flow rate is:

$Ta/Caf=0.3\ mL/\text{day}/1.6667\ mg/mL=0.18\ mL/\text{day}$

In some embodiments, the volumetric flow rate as indicated at 322 can be directly programmed into the variable rate drug delivery device. In other embodiments of the invention, a programmer device effectively recalculates the volumetric flow rate based on other data input by the user.

Display portion 324 illustrates or reports to the user the desired residual volume in the reservoir at the time of refill: We want to refill the pump when 2 mL of the mixture remains within the reservoir. Thus:

Reservoir Volume−2 mL=Refill Reservoir Volume 18 mL−2 mL=16 mL.

In display portion 326, the refill interval is displayed for the user, based on the assumption of display portion 324 and the volumetric flow rate to be administered by the pump. In order to calculate the number of days that will elapse before the next refill, we use the following calculation:

Refill Reservoir Volume/Flow Rate=Refill Interval 16 mL/0.18 mL/day=88 days

FIG. 9 illustrates another visual output display 400 for a fixed rate drug delivery device. Identical fields are identically numbered as the previously discussed fields and are not described again. In fixed rate entry field 208, a fixed, volumetric value of 0.25 milliliters per day has been entered, as indicated at 402. The drug entry portion 220 has been filled in similarly to that of FIG. 6, with a 0.3 milligrams per day desired dose rate being entered for morphine as indicated at 404.

FIG. 10 illustrates the calculation results for the fixed flow rate embodiment. In display output 420, a drug composition portion 422 illustrates that 5.6 milliliters of saline, a diluent, has been specified for addition to the mixture because of the use of the fixed rate pump, indicated at 424. In the event that the user specified saline as one of the drugs in the mixture, an advisory is presented at 426, explaining the duplicate appearance of saline. The flow rate, indicated at 264, is the flow rate as entered by the user for the fixed rate pump.

Another computer program method provided by present invention may be described. The present invention provides a computer program method for determining a new daily drug dose for one drug without changing the mixture in the implantable device. In one such method, the previously stored data for a patient can be retrieved using a patient ID and a physician ID. The previously stored data can include the date of last device refill, the true concentrations of each drug in the device, and the previously set mixture flow rate or dose rate of a reference drug for the device.

The date of last refill and the mixture flow rate can be used to calculate the remaining mixture volume in the implantable device. The new, desired dose rate for one the drugs in the mixture, not necessarily the reference drug, can be entered into the program. The program, using the new desired dose rate and the true drug concentrations, can calculate a new mixture flow rate or reference drug flow rate for the implantable device that will satisfy the new desired dose rate. The program preferably also calculates and outputs the dose rates of all drugs administered at the new rate and also calculates and outputs the refill interval and date of next refill at the new dose rate. This aspect of the invention allows for adjustment of the dose rate of one drug as desired, without requiring the emptying and refilling of the implantable device reservoir.

The program can receive the true concentration of each drug in the mixture as well as the existing mixture volume in the implantable device. The true concentrations and existing mixture volume are preferably retrieved from previously stored values from a previous calculation session. The program can also receive the desired new dose rate for one of the drugs in the mixture. The program can then calculate and output the new dose rate for the reference drug, the estimated refill interval and/or date, and the dose rates for all drugs in the mixture. Some program methods calculate and output the proper volumetric flow rate for the implantable device. A programmer unit can then be used to transmit the new reference drug flow rate and/or the new volumetric flow rate to the implantable device.

A Second Set of Methods

The present invention may be implemented using another set of methods, which are described below mathematically. The variables in the equations are named and explained prior to their use. The letters A, B, C, and D are used to denote the first, second, third, and fourth drugs in the equations, respectively, and the letter X may be used to denote any one of the drugs generally. More than four drugs may of course be used in expanded versions of the equations. The units of the variables are given in brackets. In these equations, and all equations and methods of the present invention, undesirable results from equations, such as dividing by zero, are preferably guarded against by checking for zero values before dividing.

Calculations for Adjustable Flow Rate Device

DoseRateA=the desired dose rate for drug A [mass/time]

DoseRateB=the desired dose rate for drug B [mass/time]

DoseRateC=the desired dose rate for drug C [mass/time]

DoseRateD=the desired dose rate for drug D [mass/time]

DoseRateX is typically referred to as the daily dose, having units of mg/day or mcg/day.

InitConcA = the initial concentration of drug A [mass/vol]

InitConcB = the initial concentration of drug B [mass/vol]

InitConcC = the initial concentration of drug C [mass/vol]

InitConcD = the initial concentration of drug D [mass/vol]

InitConcX typically has units of mg/ml or mcg/ml.

TotalVolFlowRate = the volumetric flow rate of the total mixture [vol/time]

TotalVolFlowRate can have units of ml/day.

$$TotalVolFlowRate = (DoseRateA/InitConcA) + ((DoseRateB/InitConcB) + (DoseRateC/InitConcC) + (DoseRateD/InitConcD)$$

TrueConcA = the true concentration of drug A in the mixture [mass/vol]

TrueConcB = the true concentration of drug B in the mixture [mass/vol]

TrueConcC = the true concentration of drug C in the mixture [mass/vol]

TrueConcD = the true concentration of drug D in the mixture [mass/vol]

$$TrueConcA = DoseRateA/TotalVolFlowRate$$

$$TrueConcB = DoseRateB/TotalVolFlowRate$$

$$TrueConcC = DoseRateC/TotalVolFlowRate$$

$$TrueConcD = DoseRateD/TotalVolFlowRate$$

VolA = the volume of drug A to be added to the mixture [vol]

VolB = the volume of drug B to be added to the mixture [vol]

VolC = the volume of drug C to be added to the mixture [vol]

VolD = the volume of drug D to be added to the mixture [vol]

VolX typically has units of ml.

DesMixVol = the desired mixture volume [vol]

$$VolA = ((TrueConcA/InitConcA)) \times DesMixVol$$

$$VolB = ((TrueConcB/InitConcB)) \times DesMixVol$$

$$VolC = ((TrueConcC/InitConcC)) \times DesMixVol$$

$$VolD = ((TrueConcD/InitConcD)) \times DesMixVol$$

CalcTotalVol = the calculated total volume, which should be very close to DesMixVol. If not, the process should be stopped, as the internal check has not been satisfied.

$$CalcTotalVol = VolA + VolB + VolC + VolD$$

The above equations have provided the values for TrueConcX, which can be input to the programmer device for the reference drug. The values for VolX can be used to fill the implantable device.

Calculations for Fixed Flow Rate Device

The calculations below can be used in calculations for the fixed flow rate device. The fixed flow rate for the device, TotalVolFlowRate, can be obtained from the user. The desired dose rate for drug X, DoseRateX, can be obtained from the user. The true concentration TrueConcX for each drug X can be calculated.

$$TrueConcA = DoseRateA/TotalVolFlowRate$$

$$TrueConcB = DoseRateB/TotalVolFlowRate$$

$$TrueConcC = DoseRateC/TotalVolFlowRate$$

$$TrueConcD = DoseRateD/TotalVolFlowRate$$

The volumetric flow rate of each drug at the initial concentration can be calculated.

$$VolFlowRateA = DoseRateA/InitConcA$$

$$VolFlowRateB = DoseRateB/InitConcB$$

$$VolFlowRateC = DoseRateC/InitConcC$$

$$VolFlowRateD = DoseRateD/InitConcD$$

The desired total mixture volume, DesMixVol, can be obtained from the user. The volume of each drug, at the initial concentration of each drug, can now be calculated to add to the mixture.

$$VolA = (DesMixVol/TotalVolFlowRate) \times VolFlowRateA$$

$$VolB = (DesMixVol/TotalVolFlowRate) \times VolFlowRateB$$

$$VolC = (DesMixVol/TotalVolFlowRate) \times VolFlowRateC$$

$$VolD = (DesMixVol/TotalVolFlowRate) \times VolFlowRateD$$

The daily volumetric flow rate of the diluent, DilVolFlowRate is calculated by subtracting the daily volumetric flow rate for each drug from the total volumetric flow rate.

$$DilVolFlowRate = TotalVolFlowRate - (VolA + VolB + VolC + VolD)$$

The volume of diluent to add to the mixture, VolDil, can be calculated.

$$VolDil = (DesMixVol/TotalVolFlowRate) \times DilVolFlowRate$$

Bolus Calculation

The equations below can be used to calculate a bolus for an implantable device.

In situations where the bolus dose is specified as a mass of drug X to be delivered, the information requested is received as BolusDoseX, having units of mass. The result can include BolusVol, the volume of bolus required to delivered the desired bolus dose of drug X.

$$BolusVol = BolusDoseX/TrueConcX$$

BolusDoseA = amount of drug A in the bolus [mass]

BolusDoseB = amount of drug B in the bolus [mass]

BolusDoseC = amount of drug C in the bolus [mass]

BolusDoseD = amount of drug D in the bolus [mass]

The amount of each drug that will be contained in the bolus can also be calculated and output as below.

$$BolusDoseA = BolusVol \times TrueConcA$$

$$BolusDoseB = BolusVol \times TrueConcB$$

$$BolusDoseC = BolusVol \times TrueConcC$$

$$BolusDoseD = BolusVol \times TrueConcD$$

In some situations, the bolus information request will start with the BolusVol being given, and the bolus dose for each drug calculated and output as above.

New Desired Dose Rate Calculations for Existing Mixture

The user may also provide a new desired dose rate for a previously filled device.

NewDoseRateX=the new desired dose rate for drug X

NewTotalVolFlowRate=the new total mixture volumetric flow rate [vol/time]

$NewTotalVolFlowRate = NewDoseRateX/TrueConcX$

Now the new dose rate NewDoseRateX can be calculated for each drug X.

$NewDoseRateA = TrueConcA \times NewTotalVolFlowRate$ $NewDoseRateB = TrueConcB \times NewTotalVolFlowRate$ $NewDoseRateC = TrueConcC \times NewTotalVolFlowRate$ $NewDoseRateD = TrueConcD \times NewTotalVolFlowRate$ The residual volume remaining in the pump, ResidualVol, can be calculated by using the elapsed time since the last fill (ElapsedTime), the device initial volume (IntialVol), and the current total volumetric flow rate (CurrentTotalVolFlowRate).

$ResidualVol = InitialVol - (CurrentTotalVolFlowRate \times ElapsedTime)$

The time of next refill, TimeOfNextRefill, can be calculated from the current time (CurrentTime) as follows, where BufferVol is the buffer of volume that is desired to remain in the device at the time of next filling. The units of time are preferably in days.

$TimeOfNextRefill = CurrentTime + ((ResidualVol - BufferVol)/NewTotalVolFlowRate)$

What is claimed is:

1. A computer program for execution in a computer device for providing information about a decision to mix at least a first drug and a second drug in an implantable drug delivery device having an adjustable flow rate, the program comprising instructions for:
   receiving a desired dose rate and an initial concentration for the first drug;
   receiving a desired dose rate and an initial concentration for the second drug;
   receiving a desired drug mixture volume for at least partial transfer to the implantable drug delivery device;
   calculating a first drug volume and a second drug volume to combine in the drug mixture, wherein the first and second drug volumes are consistent with the desired first and second drug dose rates when delivered at a proper mixture flow rate and combine to substantially fill the desired mixture volume;
   calculating the first drug true concentration in the drug mixture; and
   outputting the calculated first and second drug volumes and the first drug true concentration in the mixture.

2. A computer program as in claim 1, further comprising instructions for calculating a second drug true concentration.

3. A computer program as in claim 1, further comprising instructions for calculating and outputting the proper mixture flow rate for the implantable drug delivery device.

4. A computer program as in claim 1, further comprising instructions for outputting a dose rate for the second drug.

5. A computer program as in claim 1, wherein the calculating first drug true concentration includes calculating the formula $Caf = (Cai \times Cbi)/((Cbi + (Tb/Ta) \times Cai),$ wherein Caf represents the true concentration of the first drug,
Cai represents the initial concentration of the first drug,
Cbi represents the initial concentration of the second drug,
Ta represents the desired dose rate for the first drug, and
Tb represents the desired dose rate for the second drug.

6. A computer program as in claim 2, wherein the calculating second drug true concentration includes calculating the formula $Cbf = (Ta/Tb) \times Caf,$ wherein Cbf represents the true concentration of the second drug,
Caf represents the true concentration of the first drug,
Ta represents the desired dose rate for the first drug, and
Tb represents the desired dose rate for the second drug.

7. A computer program as in claim 3, wherein the calculating proper mixture flow rate includes calculating the formula $FlowMix = Ta/Caf;$ wherein FlowMix represents the Flow rate for the mixture,
Caf represents the true concentration of the first drug, and
Ta represents the desired dose rate for the first drug.

8. A computer program as in claim 1, wherein the calculating volume includes calculating the formula:

$Vai = (Caf/Cai) \times MixVol;$ and $Vbi = (Cbf/Cbi) \times MixVol;$ wherein Vai represents the volume of the first drug to add to the mixture,
Vbi represents the volume of the second drug to add to the mixture
Caf represents the true concentration of the first drug,
Cai represents the initial concentration of the first drug,
Cbf represents the true concentration of the second drug,
Cbi represents the initial concentration of the second drug, and
MixVol represents the total volume of the mixture.

9. A computer program as in claim 1, further comprising instructions for receiving an implantable drug delivery device reservoir size and for calculating a refill interval as a function of the reservoir size and the desired dose rates.

10. A computer program as in claim 1, further comprising instructions for calculating and outputting a bolus dose and volume for each drug in the mixture.

11. A computer program as in claim 1, further comprising instructions for outputting the calculations used in the calculating of claim 1.

12. A computer program as in claim 1, wherein the drugs are selected from the group consisting of morphine, baclofen, clonidine, bupivacaine, and adrenaline.

13. A computer program as in claim 1, further comprising instructions for receiving drug names into a drug name list and instructions allowing a user to modify the drug name list.

14. A computer program for execution in a computer device for providing information about a decision to mix at least a first drug and a second drug in an implantable drug delivery device having a fixed flow rate, the program comprising instructions for:
  receiving the fixed flow rate;
  receiving a desired dose rate and an initial concentration for the first drug;
  receiving a desired dose rate and an initial concentration for the second drug;
  receiving a desired drug mixture volume for at least partial transfer to the implantable drug delivery device;
  calculating a first drug volume, a second drug volume, and a diluent volume to combine in the drug mixture, wherein the first drug, second drug, and diluent volumes are consistent with the desired first and second drug dose rates when delivered at the fixed flow rate, and combine to substantially fill the desired mixture volume;
  calculating the first drug true concentration in the drug mixture; and
  outputting the calculated first drug, second drug, and diluent volumes and the first drug true concentration in the mixture.

15. A computer program as in claim 14, further comprising instructions for calculating a second drug true concentration.

16. A computer program as in claim 14, further comprising instructions for calculating and outputting a dose rate for the second drug.

17. A computer program as in claim 14, further comprising instructions for receiving an implantable drug delivery device reservoir size and for calculating and outputting a refill interval for the implantable device.

18. A computer program as in claim 14, further comprising instructions for outputting the calculations used in the calculating of claim 14.

19. A computer program as in claim 14, wherein the drugs are selected from the group consisting of morphine, baclofen, clonidine, bupivacaine, and adrenaline.

20. In an implantable drug delivery system including an implantable drug deliver device having an adjustable flow rate and a reservoir volume, a programmer device for setting the adjustable flow rate via telemetry, and a computer device for executing a computer program having instructions, a method for setting the adjustable flow rate comprising:
  entering into the computer device a desired dose rate and initial concentration for a first drug;
  entering into the computer a desired dose rate and initial concentration for a second drug;
  entering into the computer the reservoir volume for the implantable drug delivery device;
  executing the computer program instructions in the computer to calculate and output a first drug amount and a second drug amount to combine to form a drug mixture having a mixture volume, wherein the first and second drug amounts are consistent with the first and second drug desired dose rates and wherein the mixture volume is sufficient to at least substantially fill the reservoir;
  executing the computer program in the computer to calculate and output a first drug true concentration in the drug mixture;
  entering the first drug true concentration in the programmer device;
  entering the first drug desired dose rate into the programmer device;
  combining the first and second drug amounts into the mixture in the implantable device; and
  transmitting a flow rate to satisfy the first drug desired dose rate to the implantable device using the programmer device.

21. A method as in claim 20, further comprising calculating and outputting a second drug dose rate.

22. A method as in claim 20, further comprising calculating and outputting volumetric flow rates for the first drug and the second drug.

23. A method as in claim 20, further comprising calculating and outputting a second drug true concentration in the mixture.

24. A method as in claim 20, further comprising executing computer program instructions in the computer for visually outputting the calculations used to determine the outputs of claim 1.

25. A method as in claim 20, wherein the programmer device and the computer device are the same device.

26. A method as in claim 20, wherein the programmer device and the computer device are different devices.

27. A method as in claim 20, further comprising obtaining a desired dose rate and initial concentration for a third drug and executing computer program instructions to calculate a third drug amount to add to the mixture, wherein the first, second, and third drug amounts are consistent with the desired dose rates of the first, second, and third drugs.

28. A computer program for execution in a computer device for providing information about a decision to change the dose rate of one drug in an implantable device having an adjustable flow rate and having a mixture including at least a first drug and a second drug, the program comprising instructions for:
  receiving an existing mixture volume in the implantable device;
  receiving existing true concentrations of the first drug and the second drug in the mixture;
  receiving a desired dose rate of a selected one of the drugs in the mixture; and
  calculating and outputting a proper mixture flow rate for the implantable drug delivery device consistent with the existing mixture and the desired dose rate of the selected drug in the mixture.

29. A computer program as in claim 28, further comprising instructions for calculating and outputting a refill interval for the implantable device.

30. A computer program as in claim 28, further comprising instructions for calculating and outputting a reference dose rate for a drug selected as a reference drug from among the drugs in the mixture, where the selected reference drug is not the same drug as the drug having the desired dose rate.

31. A computer program as in claim 28, further comprising instructions for outputting the calculations used in the calculating of claim 28.

32. A computer program as in claim 28, wherein the receiving existing true concentrations of the first drug and the second drug in the mixture includes retrieving previously stored true concentrations.

33. A computer program as in claim 28, wherein the receiving an existing mixture volume in the implantable device includes retrieving a previously stored previous mixture volume, previous mixture flow rate, and previous fill date, and calculating the mixture volume as a function of the previous mixture volume, previous mixture flow rate, and previous fill date.

34. A computer program for execution in a computer device for providing information about a decision to mix at least a first drug and a second drug in a drug delivery device having an adjustable flow rate, the program comprising instructions for:
- receiving a desired dose rate and an initial concentration for the first drug;
- receiving a desired dose rate and an initial concentration for the second drug;
- receiving a desired drug mixture volume for at least partial transfer to the drug delivery device;
- calculating a first drug volume and a second drug volume to combine in the drug mixture, wherein the first and second drug volumes are consistent with the desired first and second drug dose rates when delivered at a proper mixture flow rate and combine to substantially fill the desired mixture volume;
- calculating the first drug true concentration in the drug mixture; and
- outputting the calculated first and second drug volumes and the first drug true concentration in the mixture.

35. A computer program as in claim 34, further comprising instructions for calculating a second drug true concentration.

36. A computer program as in claim 34, further comprising instructions for calculating and outputting the proper mixture flow rate for the drug delivery device.

37. A computer program as in claim 34, further comprising instructions for outputting a dose rate for the second drug.

38. A computer program as in claim 34, further comprising instructions for receiving a drug delivery device reservoir size and for calculating a refill interval as a function of the reservoir size and the desired dose rates.

39. A computer program as in claim 34, further comprising instructions for calculating and outputting a bolus dose and volume for each drug in the mixture.

40. A computer program as in claim 34, further comprising instructions for outputting the calculations used in the calculating of claim 34.

41. A computer program for execution in a computer device for providing information about a decision to mix at least a first drug and a second drug in a drug delivery device having a fixed flow rate, the program comprising instructions for:
- receiving the fixed flow rate:
- receiving a desired dose rate and an initial concentration for the first drug;
- receiving a desired dose rate and an initial concentration for the second drug;
- receiving a desired drug mixture volume for at least partial transfer to the drug delivery device;
- calculating a first drug volume, a second drug volume, and a diluent volume to combine in the drug mixture, wherein the first drug, second drug, and diluent volumes are consistent with the desired first and second drug dose rates when delivered at the fixed flow rate, and combine to substantially fill the desired mixture volume;
- calculating the first drug true concentration in the drug mixture; and
- outputting the calculated first drug, second drug, and diluent volumes and the first drug true concentration in the mixture.

42. A computer program as in claim 41, further comprising instructions for calculating a second drug true concentration.

43. A computer program as in claim 41, further comprising instructions for calculating and outputting a dose rate for the second drug.

44. A computer program as in claim 41, further comprising instructions for receiving a drug delivery device reservoir size and for calculating and outputting a refill interval for the drug delivery device.

45. A computer program as in claim 41, further comprising instructions for outputting the calculations used in the calculating of claim 41.

* * * * *